United States Patent
Cattenhead

(12) 
(10) Patent No.: US 7,726,526 B2
(45) Date of Patent: Jun. 1, 2010

(54) LATEX GLOVE REMOVAL AND DISPOSAL DEVICE

(76) Inventor: Kevin Cattenhead, 6850 Boeing Ave., Fontana, CA (US) 92336

(*) Notice: Subject to any disclaimer, the term of this patent is extended or adjusted under 35 U.S.C. 154(b) by 0 days.

(21) Appl. No.: 09/844,613

(22) Filed: Apr. 27, 2001

(65) Prior Publication Data

US 2002/0158092 A1 Oct. 31, 2002

(51) Int. Cl.
*A47G 25/80* (2006.01)
(52) U.S. Cl. ....................................... 223/111
(58) Field of Classification Search ................ 223/111; 220/908
See application file for complete search history.

(56) References Cited

U.S. PATENT DOCUMENTS

D335,565 S * 5/1993 Juergens ...................... D34/10
6,241,134 B1 * 6/2001 Dunkel ........................ 223/111

* cited by examiner

*Primary Examiner*—John J. Calvert
(74) *Attorney, Agent, or Firm*—Goldstein & Lavas, P.C.

(57) ABSTRACT

A latex glove removal and disposal device including a container having an open upper end, a closed lower end, a front wall, a back wall, and opposed side walls. A cover member is dimensioned for positioning over the open upper end of the container. The cover member has a closed upper end, an open lower end, a front wall, a back wall, and opposed side walls. The front wall of the cover member has an opening therethrough. A glove removal apparatus is secured to the container and is positionable between a person's wrist and an opening of a latex glove to facilitate removal of the latex glove from the person's hand.

5 Claims, 2 Drawing Sheets

LATEX GLOVE REMOVAL AND DISPOSAL DEVICE

BACKGROUND OF THE INVENTION

The present invention relates to a latex glove removal and disposal device and more particularly pertains to facilitating a sanitary removal of a latex glove from a hand.

The use of storage receptacles is known in the prior art. More specifically, storage receptacles heretofore devised and utilized for the purpose of containing items for disposal are known to consist basically of familiar, expected and obvious structural configurations, notwithstanding the myriad of designs encompassed by the crowded prior art which have been developed for the fulfillment of countless objectives and requirements.

While these devices fulfill their respective, particular objective and requirements, these patents do not describe a latex glove removal and disposal device for facilitating a sanitary removal of a latex glove from a hand.

In this respect, the latex glove removal and disposal device according to the present invention substantially departs from the conventional concepts and designs of the prior art, and in doing so provides an apparatus primarily developed for the purpose of facilitating a sanitary removal of a latex glove from a hand.

Therefore, it can be appreciated that there exists a continuing need for a new and improved latex glove removal and disposal device which can be used for facilitating a sanitary removal of a latex glove from a hand. In this regard, the present invention substantially fulfills this need.

SUMMARY OF THE INVENTION

In the view of the foregoing disadvantages inherent in the known types of storage receptacles now present in the prior art, the present invention provides an improved latex glove removal and disposal device. As such, the general purpose of the present invention, which will be described subsequently in greater detail, is to provide a new and improved latex glove removal and disposal device which has all the advantages of the prior art and none of the disadvantages.

To attain this, the present invention essentially comprises a container having a generally rectangular configuration. The container has an open upper end, a closed lower end, a front wall, a back wall, and opposed side walls. The closed lower end has an enlarged base secured thereto. The opposed side walls each have a metal bar extending outwardly therefrom downwardly of the open upper end. A cover member is dimensioned for positioning over the open upper end of the container. The cover member has a closed upper end, an open lower end, a front wall, a back wall, and opposed side walls. The front wall of the cover member has an opening therethrough. The closed upper end has a transparent window therein. The opposed side walls of the cover member each have a magnetic bar extending outwardly therefrom adjacent to the open lower end for mating with the metal bars of the container in a closed orientation. A glove removal apparatus is secured to the container. The glove removal apparatus has a generally inverted L-shaped configuration defined by a lower vertical member and an upper horizontal member. The lower vertical member is secured to the front wall of the container. The upper horizontal member is disposed over the open upper end of the container. The upper horizontal member tapers outwardly to a pointed free end that is positionable between a person's wrist and an opening of a latex glove to facilitate removal of the latex glove from the person's hand.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved latex glove removal and disposal device which has all the advantages of the prior art storage receptacles and none of the disadvantages.

It is another object of the present invention to provide a new and improved latex glove removal and disposal device which may be easily and efficiently manufactured and marketed.

It is a further object of the present invention to provide a new and improved latex glove removal and disposal device which is of durable and reliable construction.

An even further object of the present invention is to provide a new and improved latex glove removal and disposal device which is susceptible of a low cost of manufacture with regard to both materials and labor, and which accordingly is then susceptible of low prices of sale to the consuming public, thereby making such a latex glove removal and disposal device economically available to the buying public.

Even still another object of the present invention is to provide a new and improved latex glove removal and disposal device for facilitating a sanitary removal of a latex glove from a hand.

Lastly, it is an object of the present invention to provide a new and improved latex glove removal and disposal device including a container having an open upper end, a closed lower end, a front wall, a back wall, and opposed side walls. A cover member is dimensioned for positioning over the open upper end of the container. The cover member has a closed upper end, an open lower end, a front wall, a back wall, and opposed side walls. The front wall of the cover member has an opening therethrough. A glove removal apparatus is secured to the container and is positionable between a person's wrist and an opening of a latex glove to facilitate removal of the latex glove from the person's hand.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
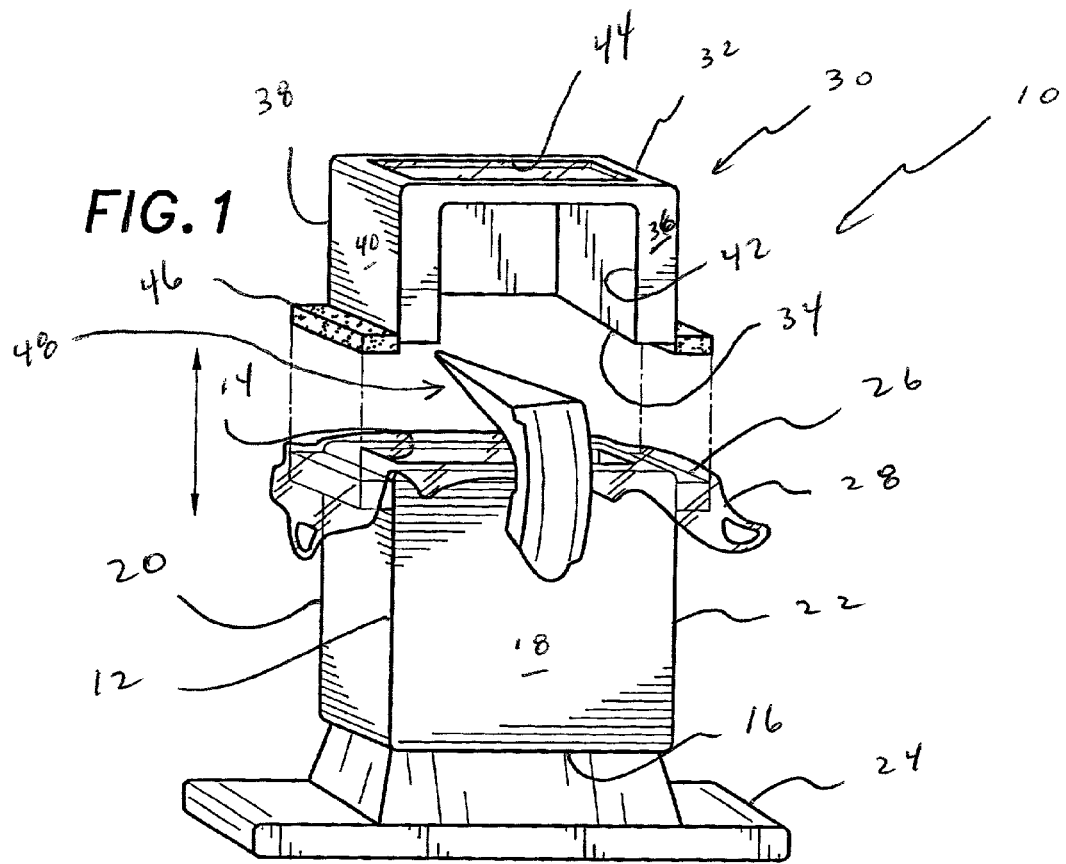
FIG. 1 is a perspective view of the preferred embodiment of the latex glove removal and disposal device constructed in accordance with the principles of the present invention.
Figure 2:
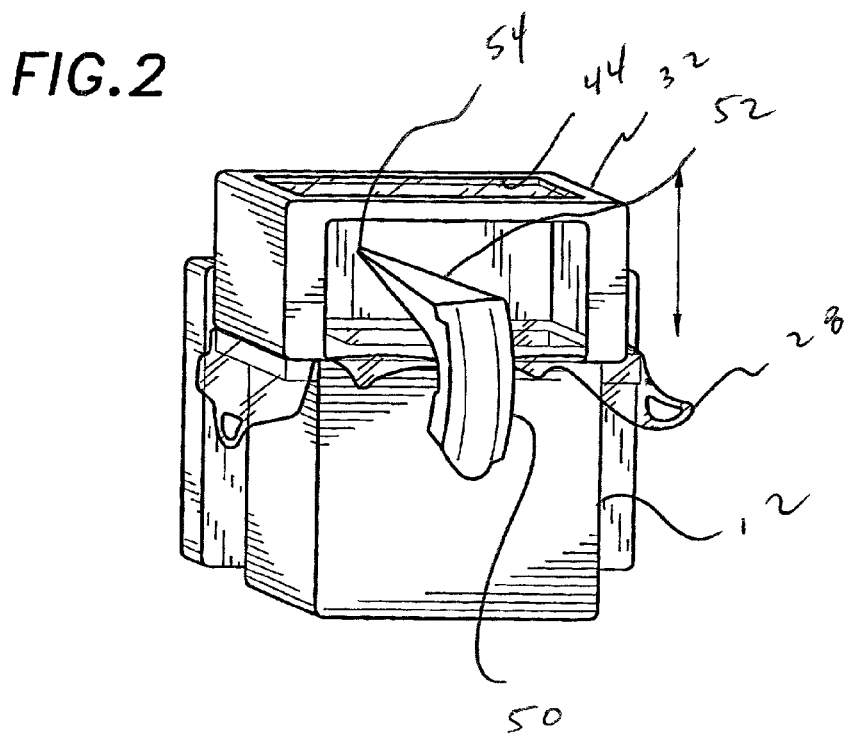
FIG. 2 is a perspective view of an alternate design of the present invention.
Figure 4:
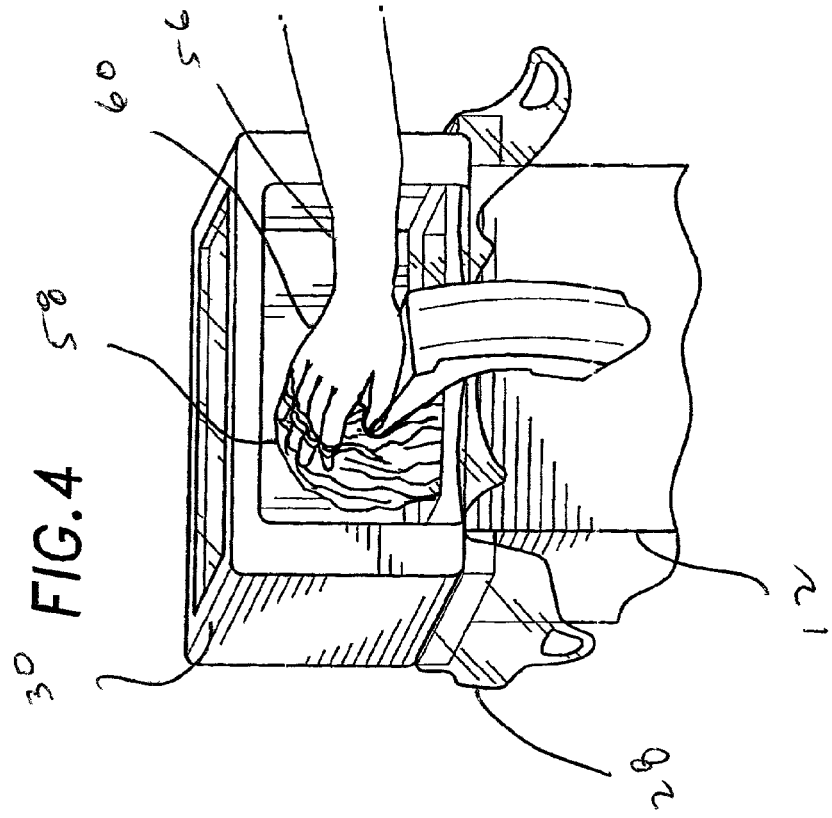
FIGS. 3 and 4 are perspective views of the present invention illustrated in use.
Figure 3:
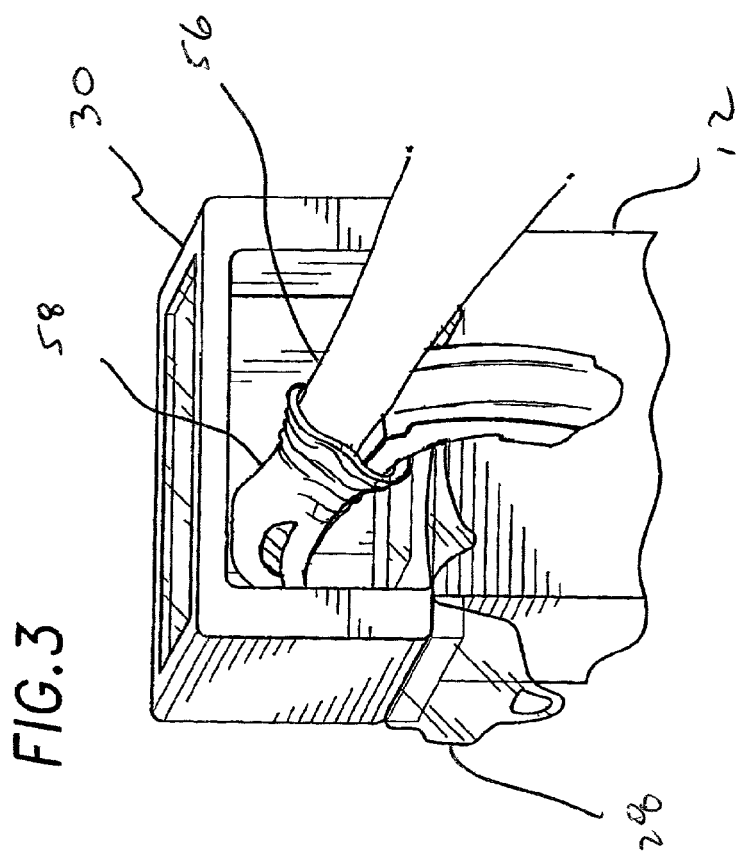

With reference now to the drawings, and in particular, to FIGS. 1 through 4 thereof, the preferred embodiment of the new and improved latex glove removal and disposal device embodying the principles and concepts of the present invention and generally designated by the reference number 10 will be described.

Specifically, it will be noted in the various Figures that the device relates to a latex glove removal and disposal device for facilitating a sanitary removal of a latex glove from a hand. In its broadest context, the device consists of a container, a cover member, and a glove removal apparatus. Such components are individually configured and correlated with respect to each other so as to attain the desired objective.

The container 12 has a generally rectangular configuration. The container 12 has an open upper end 14, a closed lower end 16, a front wall 18, a back wall 20, and opposed side walls 22. The closed lower end 16 has an enlarged base 24 secured thereto. Note FIG. 1. This configuration allows the container 12 to be freestanding. An alternate design for the present invention, as illustrated in figure two, is absent the enlarged base, but instead is mountable on a wall or other suitable recipient surface. The opposed side walls 22 each have a metal bar 26 extending outwardly therefrom downwardly of the open upper end 14. In use, a disposable plastic bag 28 is positionable within the container 12.

The cover member 30 is dimensioned for positioning over the open upper end 14 of the container 12. The cover member 30 has a closed upper end 32, an open lower end 34, a front wall 36, a back wall 38, and opposed side walls 40. The front wall 36 of the cover member 30 has an opening 42 therethrough. The closed upper end 32 has a transparent window 44 therein. The opposed side walls 40 of the cover member 30 each have a magnetic bar 46 extending outwardly therefrom adjacent to the open lower end 34 for mating with the metal bars 26 of the container 12 in a closed orientation. In use, the cover member 30 is positioned over the container 12 whereby the magnetic bars 46 and the metal bars mate with the plastic bag 28 sandwiched therebetween.

The glove removal apparatus 48 is secured to the container 12. The glove removal apparatus 48 has a generally inverted L-shaped configuration defined by a lower vertical member 50 and an upper horizontal member 52. The lower vertical member 50 is secured to the front wall 18 of the container 12. The upper horizontal member 52 is disposed over the open upper end 14 of the container 12. The upper horizontal member 52 tapers outwardly to a pointed free end 54 that is positionable between a person's wrist 56 and an opening of a latex glove 58 to facilitate removal of the latex glove 58 from the person's hand 60. Note FIGS. 3 and 4. Thus, a person places their hand 60 through the opening 42 in the front wall 36 of the cover member 30 and then positions the pointed free end 54 within the opening of the latex glove 58 whereupon the user slides his arm rearwardly to separate the glove 58 from their hand 60. The glove 58 will fall safely into the plastic bag 28 for its later disposal. All of this is accomplished without the user making contact with the glove 58 with exposed skin.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A latex glove removal and disposal device for facilitating a sanitary removal of a latex glove from a hand comprising, in combination:

a container having a generally rectangular configuration, the container having an open upper end, a closed lower end, a front wall, a back wall, and opposed side walls, the closed lower end having an enlarged base secured thereto, the opposed side walls each having a metal bar extending outwardly therefrom downwardly of the open upper end;

a cover member dimensioned for positioning over the open upper end of the container, the cover member having a closed upper end, an open lower end, a front wall, a back wall, and opposed side walls, the front wall of the cover member having an opening therethrough, the closed upper end having a transparent window therein, the opposed side walls of the cover member each having a magnetic bar extending outwardly therefrom adjacent to the open lower end for mating with the metal bars of the container in a closed orientation; and a glove removal apparatus secured to the container, the glove removal apparatus having a generally inverted L-shaped configuration defined by a lower vertical member and an upper horizontal member, the lower vertical member secured to the front wall of the container, the upper horizontal member being disposed over the open upper end of the container, the upper horizontal member tapering outwardly to a pointed free end that is positionable between a person's wrist and an opening of a latex glove to facilitate removal of the latex glove from the person's hand.

2. A latex glove removal and disposal device for facilitating a sanitary removal of a latex glove from a hand comprising, in combination:

a container having an open upper end, a closed lower end, a front wall, a back wall, and opposed side walls, the opposed side walls each having a metal bar extending outwardly therefrom downwardly of the open upper end;

a cover member dimensioned for positioning over the open upper end of the container, the cover member having a closed upper end, an open lower end, a front wall, a back wall, and opposed side walls, the front wall of the cover member having an opening therethrough, and the opposed side walls each having a magnetic bar adjacent to the open lower end for mating with the metal bars of the container in a closed orientation; and a glove removal apparatus secured to the container that is positionable between a person's wrist and an opening of a latex glove to facilitate removal of the latex glove from the person's hand.

3. A latex glove removal and disposal device for facilitating a sanitary removal of a latex glove from a hand comprising, in combination:

a container having an open upper end, a closed lower end, a front wall, a back wall, and opposed side walls;

a cover member dimensioned for positioning over the open upper end of the container, the cover member having a closed upper end, an open lower end, a front wall, a back wall, and opposed side walls, the front wall of the cover member having an opening there through, the closed upper end having a transparent window therein; and a glove removal apparatus secured to the container that is positionable between a person's wrist and an opening of a latex glove to facilitate removal of the latex glove from the person's hand.

4. A latex glove removal and disposal device for facilitating a sanitary removal of a latex glove from a hand comprising, in combination:

a container having an open upper end, a closed lower end, a front wall, a back wall, and opposed side walls;

a cover member dimensioned for positioning over the open upper end of the container, the cover member having a closed upper end, an open lower end, a front wall, a back wall, and opposed side walls, the front wall of the cover member having an opening therethrough; and a glove removal apparatus secured to the container that is positionable between a person's wrist and an opening of a latex glove to facilitate removal of the latex glove from the person's hand, the glove removal apparatus having a generally inverted L-shaped configuration defined by a lower vertical member and an upper horizontal member, the lower vertical member secured to the front wall of the container, the upper horizontal member being disposed over the open upper end of the container.

5. The latex glove removal and disposal device as set forth in claim 4, wherein the upper horizontal member tapers outwardly to a pointed free end that is positionable between a person's wrist and an opening of a latex glove to facilitate removal of the latex glove from the person's hand.

* * * * *